(12) United States Patent
Lozano Platonoff et al.

(10) Patent No.: US 10,799,643 B2
(45) Date of Patent: Oct. 13, 2020

(54) DRIVE-CONTROL SYSTEM FOR AN INJECTION DEVICE

(71) Applicant: COPERNICUS SP. Z O.O., Szczecin (PL)

(72) Inventors: Alberto Lozano Platonoff, Szczecin (PL); Mateusz Wilczek, Szczecin (PL); Adam Stefanski, Gniezno (PL)

(73) Assignee: COPERNICUS SP. Z O.O., Szczecin (PL)

( * ) Notice: Subject to any disclaimer, the term of this patent is extended or adjusted under 35 U.S.C. 154(b) by 99 days.

(21) Appl. No.: 16/065,260

(22) PCT Filed: Dec. 21, 2016

(86) PCT No.: PCT/IB2016/057856
§ 371 (c)(1),
(2) Date: Jun. 22, 2018

(87) PCT Pub. No.: WO2017/109713
PCT Pub. Date: Jun. 29, 2017

(65) Prior Publication Data
US 2019/0054248 A1 Feb. 21, 2019

(30) Foreign Application Priority Data
Dec. 22, 2015 (PL) ........................................ P415473

(51) Int. Cl.
*A61M 5/315* (2006.01)
*A61M 5/20* (2006.01)

(52) U.S. Cl.
CPC .......... *A61M 5/31551* (2013.01); *A61M 5/20* (2013.01); *A61M 5/2033* (2013.01);
(Continued)

(58) Field of Classification Search
CPC .. A61M 5/20; A61M 5/2033; A61M 5/31505; A61M 5/31536; A61M 5/31541;
(Continued)

(56) References Cited

U.S. PATENT DOCUMENTS

| 533,575 A | 2/1895 | John |
| 2,444,570 A | 8/1946 | Lawrence et al. |

(Continued)

FOREIGN PATENT DOCUMENTS

| DE | 3609555 | 9/1987 |
| EP | 0295075 | 12/1991 |

(Continued)

*Primary Examiner* — Jason E Flick
(74) *Attorney, Agent, or Firm* — Browdy and Neimark, PLLC

(57) ABSTRACT

A drive-control system for an injection device for delivering settable doses of a pharmaceutical substance contained in a cartridge (3), the system comprising a tubular housing body (2) having a longitudinal axis (A-A), a proximal end (2a) and a distal end (2b) connectable to the cartridge enclosure (3), the system further comprising a helical spring (7) contained in the housing body and a piston rod (6) moveable towards said distal end (2b) and blocked in translation towards the proximal end (2a). The housing body (2) further contains (i) a control sleeve (10) on which the spring (7) is mounted, the control sleeve (10) being rotatable around the axis (A-A), and (ii) a setting sleeve (11) translatable along the axis (A-A), wherein rotation of the control sleeve (10) in a first direction combined with compression of the spring (7) causes the setting sleeve (11) to be translated towards the proximal end (2a) of the housing body (2), and extension of the spring (7) causes the setting sleeve (11) to be translated towards the distal end (2b) of the housing body (2) and the control sleeve (10) to be rotated in a second direction and the piston rod (6) to be pushed towards the outside of the (Continued)

housing body (2). An injection device comprising the drive-control system according to the invention.

19 Claims, 12 Drawing Sheets

(52) U.S. Cl.
CPC ...... *A61M 5/3155* (2013.01); *A61M 5/31505* (2013.01); *A61M 5/31536* (2013.01); *A61M 5/31541* (2013.01); *A61M 5/31553* (2013.01); *A61M 5/31578* (2013.01)

(58) Field of Classification Search
CPC ............ A61M 5/3155; A61M 5/31551; A61M 5/31553; A61M 5/31578; A61M 5/178; A61M 5/315; A61M 5/31; A61M 5/31533; A61M 5/31545; A61M 5/31548; A61M 5/31565; A61M 5/31576
USPC .......................................................... 604/209
See application file for complete search history.

(56) References Cited

U.S. PATENT DOCUMENTS

| | | | |
|---|---|---|---|
| 2,717,597 A | 12/1952 | Hein, Jr. | |
| 4,470,317 A | 9/1984 | Sabloewski et al. | |
| 4,498,904 A | 9/1985 | Turner et al. | |
| 5,304,152 A | 4/1994 | Sams et al. | |
| 5,320,609 A | 6/1994 | Haber et al. | |
| 5,480,387 A | 1/1996 | Gabriel et al. | |
| 5,505,704 A | 4/1996 | Pawelka | |
| 5,626,566 A | 5/1997 | Peterson | |
| 5,674,204 A | 10/1997 | Chanoch et al. | |
| 5,688,251 A | 11/1997 | Chanoch et al. | |
| 6,083,197 A | 7/2000 | Umbaugh | |
| 6,221,046 B1 | 4/2001 | Burroughs et al. | |
| 6,899,698 B2 | 5/2005 | Sams et al. | |
| 7,896,850 B2 | 3/2011 | Kronestedt | |
| 7,918,833 B2 | 3/2011 | Veasey | |
| 8,357,120 B2 | 1/2013 | Petersen | |
| 8,376,993 B2 | 2/2013 | Cox et al. | |
| 8,512,297 B2 | 8/2013 | Veasey | |
| 8,603,044 B2 | 12/2013 | Veasey | |
| 8,608,708 B2 | 12/2013 | Cowe | |
| 8,617,109 B2 | 12/2013 | Kronestedt et al. | |
| 8,663,167 B2 | 3/2014 | Bartha | |
| 8,679,069 B2 | 3/2014 | Veasey | |
| 8,684,969 B2 | 4/2014 | Moller | |
| 8,915,889 B2 | 12/2014 | Cox et al. | |
| 8,920,383 B2 | 12/2014 | Enggaard | |
| 8,992,486 B2 | 3/2015 | Veasey | |
| 9,011,386 B2 | 4/2015 | Kronestedt | |
| 9,011,391 B2 | 4/2015 | Veasey | |
| 9,022,994 B2 | 5/2015 | Moser | |
| 9,044,548 B2 | 6/2015 | Miller | |
| 9,095,658 B2 | 8/2015 | Wieselblad | |
| 9,138,542 B2 | 9/2015 | Smith | |
| 9,205,195 B2 | 12/2015 | Burren et al. | |
| 9,233,211 B2 | 1/2016 | Veasey | |
| 9,408,979 B2 | 8/2016 | Veasey | |
| 9,415,165 B2 | 8/2016 | Cowe | |
| 9,526,844 B2 | 12/2016 | Veasey | |
| 9,561,333 B2 | 2/2017 | Cox et al. | |
| 9,566,386 B2 | 2/2017 | Stefanski | |
| 9,623,190 B2 | 4/2017 | Veasey | |
| 9,687,611 B2 | 6/2017 | Moeller | |
| 9,775,954 B2 | 10/2017 | Veasey | |
| 2002/0052578 A1 | 5/2002 | Moller | |
| 2004/0059299 A1 | 5/2004 | Moller | |
| 2006/0276753 A1 | 12/2006 | Kronestedt | |
| 2007/0129687 A1 | 6/2007 | Marshall | |
| 2009/0054851 A1 | 2/2009 | Radmer | |
| 2009/0227955 A1 | 9/2009 | Hirschel | |
| 2010/0010454 A1* | 1/2010 | Marshall | A61M 5/2033 604/208 |
| 2010/0298781 A1 | 11/2010 | Hogdahl | |
| 2011/0034878 A1 | 2/2011 | Radmer | |
| 2012/0283647 A1 | 11/2012 | Cronenberg | |
| 2015/0080812 A1 | 3/2015 | Enggaard | |
| 2015/0265776 A1 | 9/2015 | Beek | |
| 2015/0290397 A1 | 10/2015 | Wieselblad | |
| 2015/0367078 A1 | 12/2015 | Pedersen | |
| 2016/0051770 A1 | 2/2016 | Jones | |
| 2016/0121052 A1 | 5/2016 | Burren | |
| 2016/0136358 A1 | 5/2016 | Oakley | |
| 2016/0151577 A1 | 6/2016 | Newton | |
| 2016/0158456 A1* | 6/2016 | Oakley | A61M 5/31578 604/209 |
| 2016/0317752 A1 | 11/2016 | Cowe | |
| 2017/0087307 A1 | 3/2017 | Cox | |
| 2017/0100547 A1 | 4/2017 | Stefanski | |
| 2017/0119973 A1 | 5/2017 | Roervig | |
| 2017/0224924 A1 | 8/2017 | Christensen | |
| 2018/0221587 A1* | 8/2018 | Keitel | A61M 5/31551 |

FOREIGN PATENT DOCUMENTS

| | | |
|---|---|---|
| EP | 0937471 | 9/2005 |
| EP | 1728529 | 7/2008 |
| EP | 1819382 | 10/2009 |
| EP | 1909870 | 3/2011 |
| EP | 2364742 | 9/2011 |
| EP | 1694387 | 7/2012 |
| EP | 2484395 | 8/2012 |
| EP | 1885414 | 11/2012 |
| EP | 2526987 | 11/2012 |
| EP | 1885415 | 5/2013 |
| EP | 2586477 | 5/2013 |
| EP | 2586478 | 5/2013 |
| EP | 1861141 | 12/2013 |
| EP | 2722931 | 4/2014 |
| EP | 2493533 | 2/2015 |
| EP | 2488232 | 1/2016 |
| EP | 2913075 | 5/2017 |
| WO | 1991/14467 | 10/1991 |
| WO | 1999/38554 | 8/1999 |
| WO | 2002053214 | 7/2002 |
| WO | 2006045526 | 5/2006 |
| WO | 2006126902 | 11/2006 |
| WO | 2007063342 | 6/2007 |
| WO | 2008087071 | 7/2008 |
| WO | 2015197629 | 12/2015 |
| WO | 2016/016184 | 2/2016 |
| WO | 2016/041883 | 3/2016 |
| WO | 2016107790 | 7/2016 |

* cited by examiner

DRIVE-CONTROL SYSTEM FOR AN INJECTION DEVICE

The invention relates to devices for delivering liquid pharmaceutical substances by injection into patients. In particular, the invention relates to a drive-control system for an injection device for delivering settable doses of a pharmaceutical substance and an injection device equipped with such a system. The pharmaceutical substance may be any injectable pharmaceutical substance e.g. growth hormone or insulin.

The devices of the above described type are known in the art and commonly used.

WO/2010/033770 describes a medical injector for delivering settable doses of a pharmaceutical substance having a body with a displaceable plunger. The plunger is moveable in the distal direction of the injector; proximal movement of the plunger is prevented. The injector includes an actuator for setting and delivering a dose of the substance. The plunger is provided with ratchet teeth cooperating with a blocking member for preventing proximal movement of the plunger and with an engagement portion of the actuator. For setting of a dose the actuator is displaced proximally and its engagement portion by-passes successive teeth of the immobilized plunger. For delivery of a dose, a user moves the actuator distally. During this movement the engagement portion pushes the teeth of the plunger causing it to move distally. In the case of the described injector the delivery of a dose requires manual (not automatic) operation of the actuator and hence the force applied thereto as well as the speed of the application depend on the user. This is disadvantageous because the patient must regulate the force applied to the injection button single-handed, which in turn influences the speed of the injection as well as involves additional stress and discomfort during injection.

U.S. Pat. No. 7,517,334 describes a pen-type apparatus for dispensing settable doses of a medication, provided with different variants of mechanical advantage means. The medication dispensing apparatus is also provided with a spring-driven last dose locking feature. This apparatus is quite complicated and it does not enable the set dose of the medication to be dispensed automatically.

It is an objective of the invention to provide an improved drive-control system for an injection device for delivering settable doses of a pharmaceutical substance and a respective injection device, enabling automatic delivery of a medication after the dose has been set.

It is another objective of the invention to provide a drive-control system and a respective injection device driven by a helical pressure spring.

Still another objective of the invention is to provide an injection device having a simpler design than similar devices known in the art.

According to the invention a drive-control system is provided for an injection device for delivering settable doses of a pharmaceutical substance contained in a cartridge, the system comprising a tubular housing body having a longitudinal axis, a proximal end and a distal end connectable to the cartridge enclosure, the system further comprising a helical spring contained in the housing body and a piston rod moveable towards said distal end and blocked in translation towards the proximal end.

The system according to the invention is characterized in that the housing body further contains (i) a control sleeve on which the spring is mounted, the control sleeve being rotatable around said axis, and (ii) a setting sleeve translatable along said axis, wherein rotation of the control sleeve in a first direction combined with compression of the spring causes the setting sleeve to be translated towards the proximal end of the housing body, and extension of the spring causes the setting sleeve to be translated towards the distal end of the housing body and the control sleeve to be rotated in a second direction and the piston rod to be pushed towards the outside of the housing body.

Preferably, the rotatable control sleeve is threadably connected at its distal end to the setting sleeve; the setting sleeve is engaged with the internal wall of the housing body in a way preventing rotation of the setting sleeve in relation to the housing body; the setting sleeve is engaged with the piston rod in a way enabling the translation of the setting sleeve towards the proximal end of the housing body in relation to the piston rod and blocking the translation of the setting sleeve in the opposite direction in relation to the piston rod; a blocking member is provided on the distal end of the housing body, the blocking member being engaged with the piston rod in a way preventing translation of the piston rod towards the proximal end of the housing body and enabling the translation of the piston rod in the opposite direction.

The setting sleeve may be engaged with the internal wall of the housing body by means of at least one pair of complementary longitudinal guiding means.

Preferably, the at least one pair of complementary longitudinal guiding means consists of a longitudinal groove located on the internal wall of the housing body and a longitudinal projection located on the external wall of the setting sleeve.

Preferably, the piston rod is provided with at least one series of ratchet teeth directed towards the proximal end of the housing body and the setting sleeve is provided with at least one resilient pawl engaging the ratchet teeth of the piston rod.

Alternatively, the piston rod is provided with at least one series of ratchet teeth directed towards the proximal end of the housing body and the blocking member is provided with at least one resilient pawl engaging the ratchet teeth of the piston rod.

The piston rod may have a rectangular cross-section and the series of ratchet teeth may be located on its side wall.

The blocking member preferably has a form of a blocking sleeve located inside the housing body, the piston rod extending through the blocking sleeve.

The at least one resilient pawl is preferably integral with the setting sleeve.

The blocking member may have a form of a blocking sleeve located inside the housing body, the piston rod extending through the blocking sleeve, and the at least one resilient pawl may be integral with the blocking sleeve.

Preferably, the piston rod and the setting sleeve are provided with mutually cooperating blocking elements preventing the setting sleeve to be translated proximally when the piston rod extends out of the housing body by a defined distance.

The blocking element of the piston rod is preferably selected from a group comprising an enlarged proximal ending of the piston rod, a projection located at the proximal ending of the piston rod and an annular flange located at the proximal ending of the piston rod.

The blocking element of the setting sleeve is preferably a stop member projecting from the inside wall of the setting sleeve between the pawls and the proximal end of the setting sleeve.

The setting sleeve may be provided with means for engagement of the setting sleeve with the housing body and the housing body may be provided with a resilient element, the engagement means cooperating with the resilient element to selectively block and release the translation of the setting sleeve along the housing body.

Preferably, the engagement means of the setting sleeve has a form of a series of ratchet teeth that are perpendicular to the axis of the housing body and directed towards the distal end of the housing body, and the resilient element of the housing body is an arm provided with an extension to be engaged with the teeth.

The control sleeve may be provided with at least one blocking element enabling rotation of the control sleeve in relation to the housing body in one direction as well as selective blocking and releasing of the rotation of the control sleeve in the opposite direction.

Preferably, the at least one blocking element has a form of a ratchet cooperating with a triggering activating means arranged on the housing body.

Optionally, the at least one blocking element has a form of a projection cooperating with a ratchet of a triggering activating means arranged on the housing body.

According to the invention an injection device for delivering settable doses of a liquid pharmaceutical substance is provided, adapted to be coupled with a cartridge enclosure containing said substance, the distal end of the cartridge enclosure being adapted to be coupled with a disposable injection means.

The injection device according to the invention is characterized in that it is provided with the drive-control system according to the invention, and wherein
the housing body is provided with the triggering activating means and a knob, the triggering activating means and the knob cooperating with the drive-control system;
the knob is engaged with the rotatable control sleeve to enable the rotation of the control sleeve in a defined direction;
the triggering activating means enabling selective blocking and releasing of the translation of the setting sleeve towards the distal end of the housing body, wherein
when said translation is blocked, the setting sleeve may be translated towards the proximal end of the housing body and when the setting sleeve is released it is translated towards the distal end of the housing body by the action of the extending spring.

Preferably, the triggering activating means cooperates with the resilient element of the housing body and it is adapted to be placed in a first and a second position, the first position being the position of engagement of the triggering activating means with the setting sleeve by means of the extension and the second position being the position of disengagement of the triggering activating means with the setting sleeve.

According to the invention another variant of an injection device for delivering settable doses of a liquid pharmaceutical substance is also provided, adapted to be coupled with a cartridge containing said substance, the distal end of the cartridge being adapted to be coupled with a disposable injection means.

This another variant is characterized in that the injection device is provided with the drive-control system according to any of the invention, and wherein
the housing body is provided with the triggering activating means and a knob, the triggering activating means and the knob cooperating with the drive-control system;
the knob is engaged with the rotatable control sleeve to enable the rotation of the control sleeve in a defined direction;
the triggering activating means cooperates with the blocking element of the control sleeve to enable selective blocking and releasing rotation of the control sleeve in relation to the housing body in a first direction, said rotation being combined with proximal translation of the setting sleeve, and enabling rotation of the control sleeve in a second opposite direction, said direction being combined with translation of the setting sleeve towards the distal end of the housing body by the action of the extending spring.

Preferably, the triggering activating means is provided with an extension cooperating with the blocking element of the control sleeve, the blocking element being adapted to be placed in a first and a second position, the first position being the position of engagement of the extension with the blocking element and the second position being the position of disengagement of the extension with the blocking element.

The injection device according to the invention has a relatively simple construction and enables automatic delivery of a selected dose of pharmaceutical substance to a patient.

In a preferred embodiment the injection device according to the invention is provided with a feature that prevents arming of the device upon delivery of a last dose.

Preferred embodiments of the inventions are shown in the appended drawings in which:

Preferred embodiments of the inventions are shown in the appended drawings in which.

Figure 1:
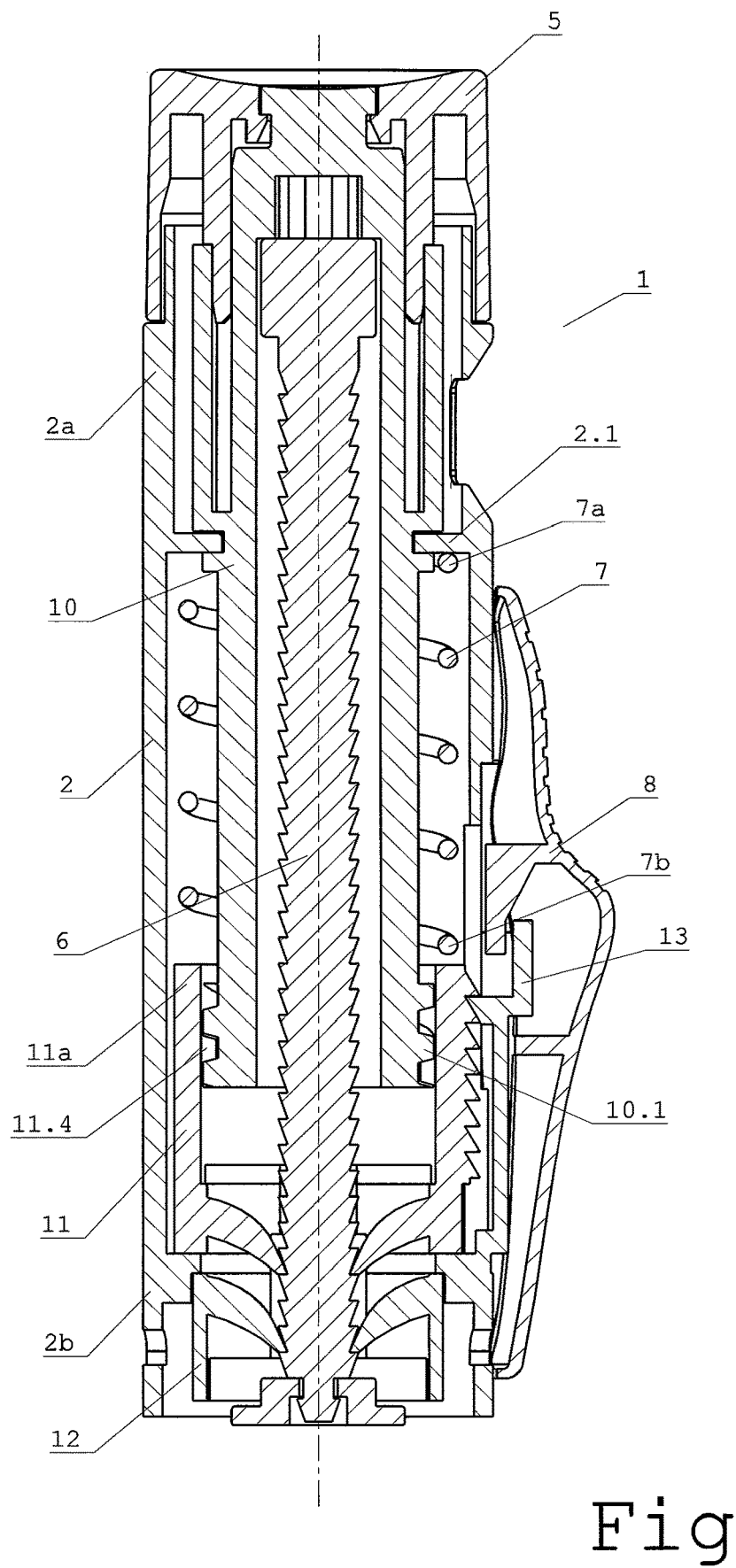
FIG. 1 shows a longitudinal sectional view of a first embodiment of the device according to the invention.
Figure 2:
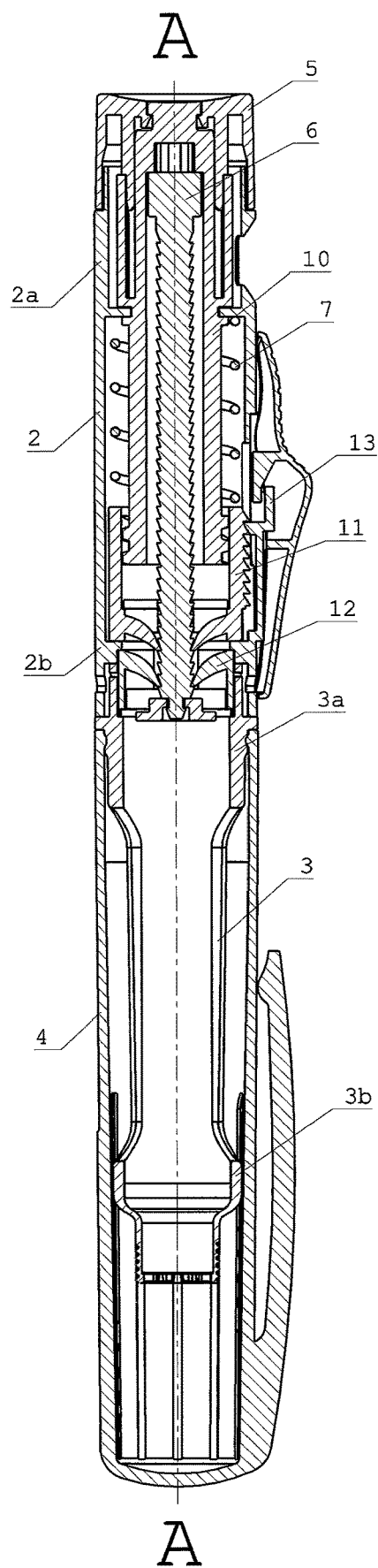
FIG. 2 shows a longitudinal sectional view of a first embodiment of the device shown in FIG. 1, with a container for a pharmaceutical substance cartridge.

The device 1 shown in FIG. 1 and FIG. 2 according to the first embodiment of the invention comprises a typical tubular housing body 2 connectable to a cartridge enclosure 3 containing a pharmaceutical substance. A protective cap 4 is fitted on the cartridge enclosure 3. The housing body 2 has a proximal end 2a on which a knob 5 is fitted and a distal end 2b which is connectable to the substance containing cartridge enclosure 3. The cartridge enclosure 3 has a distal end 3b on which a disposable injection means, in particular a hollow needle, is fitted and a proximal end 3a to be fitted to the housing body 2 of the device 1.

The terms "distal" and "proximal" are used here in relation to various elements and they should be understood as meaning respectively "the side of the end applied to a patient" and "the side of the end held by a user".

A piston rod 6 is arranged in a typical way in the housing body 2. The piston rod 6 is translated along the axis of the device 1 so as to gradually move distally within the cartridge 3 and dispense a selected dose. The axial movement of the piston rod 6 along the housing body 2 is caused by the action of a helical spring 7 arranged within the housing body 2. According to the invention a helical compression spring has been used which is an important advantage in relation to the state of art solutions in which torsional helical springs are typically used. A compression spring is easier to be produced than a torsional spring because it does not need special endings which are necessary for rotating the spring during pre-loading. Further, the helical compression spring needs fewer coils and hence it may be smaller and lighter.

Operation of the device 1 includes arming it by setting a dose by means of a knob 5, introducing the needle into the patient's body, activating the device 1 by a triggering activating means 8 which causes the dose of a pharmaceutical substance to be dispensed. As the piston rod 6 is translatable distally and blocked in proximal translation, the device may be used with only one pharmaceutical substance containing cartridge enclosure. Once the piston rod 6 has been pushed out of the housing body 2 it may not be retracted in order to allow fitting a new cartridge.

Figure 3:
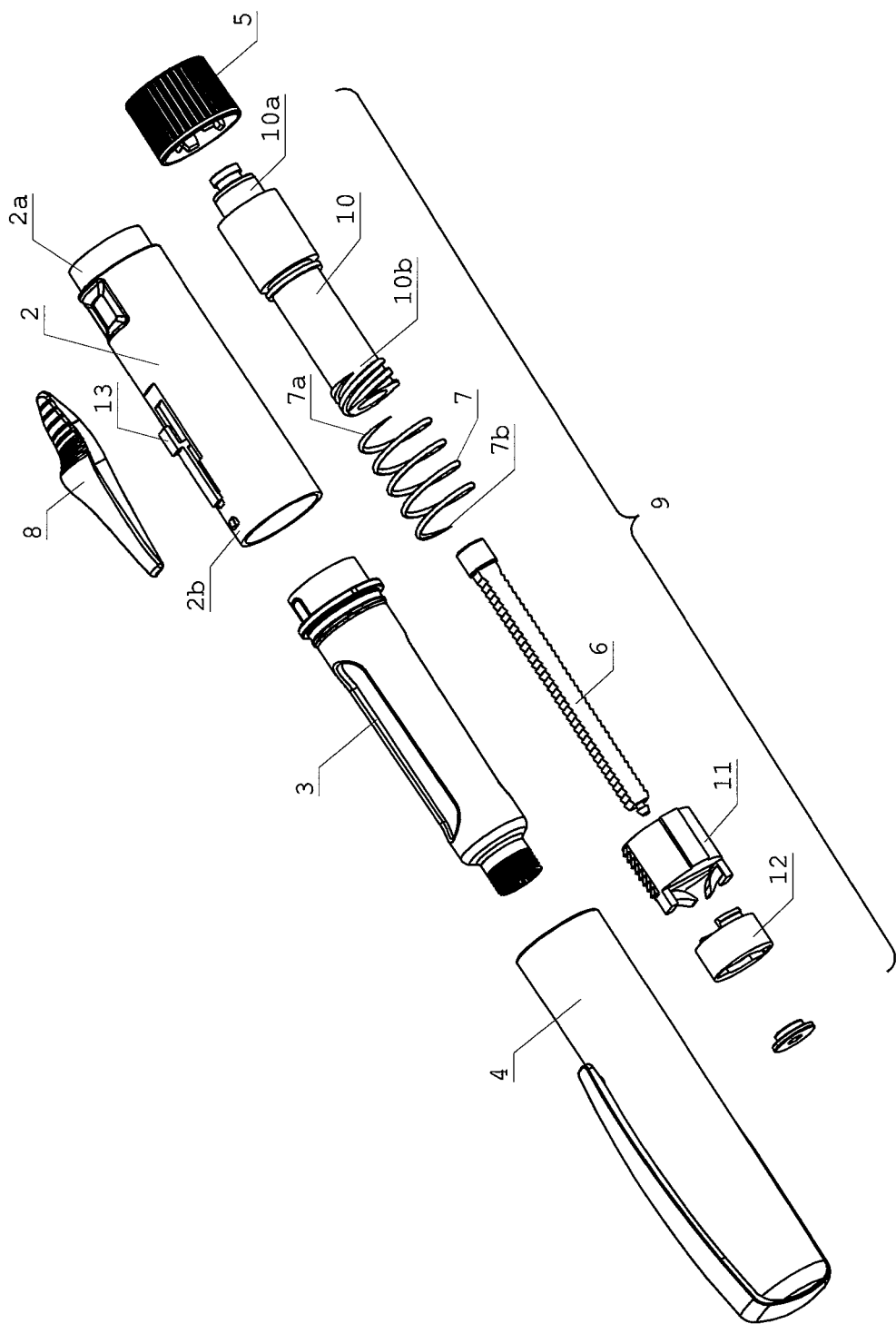
FIG. 3 shows an exploded perspective view of the device according to the first embodiment and the associated container for a pharmaceutical substance cartridge.

FIG. 3 shows an exploded view of the device 1 from the FIGS. 1 and 2 along with its parts constituting the drive-control system 9, the cartridge enclosure 3 containing a pharmaceutical substance and the cap 4.

The components shown in FIG. 3 are arranged along a common longitudinal axis A-A in the device 1. The axis A-A is the longitudinal axis of the device 1. The housing body 2 is connected at its distal end 2b with the cartridge enclosure 3. A knob 5 is mounted on the proximal end 2a of the housing body 2. The knob 5 is rotatable around the axis A-A of the housing body 2.

The drive-control system 9 of the device 1 comprises:
a control sleeve 10 rotatable within the housing body 2, the control sleeve 10 having a proximal part 10a fixed to the knob 5 and a distal part 10b on which a helical compression spring 7 is mounted;
a setting sleeve 11, threadably connected to the distal end 10b of the control sleeve 10, the setting sleeve 11 being translatable along the axis A-A in two directions;
a blocking member in the form of a blocking sleeve 12 arranged within the housing body 2 at its distal end 2b, the blocking sleeve 12 being fixed to the housing body 2;
the helical compression spring 7 abutting by its proximal end 7a a projection 2.1 located inside the housing body 2 and by its distal end 7b a proximal end 11a of the setting sleeve 11;
the piston rod 6 extending along the axis A-A is arranged within the housing body 2, the control sleeve 10, the setting sleeve 11 and the blocking sleeve 12. The piston rod 6 is distally translatable along the axis A-A of the system 9 and proximally non-translatable.

Figure 4:
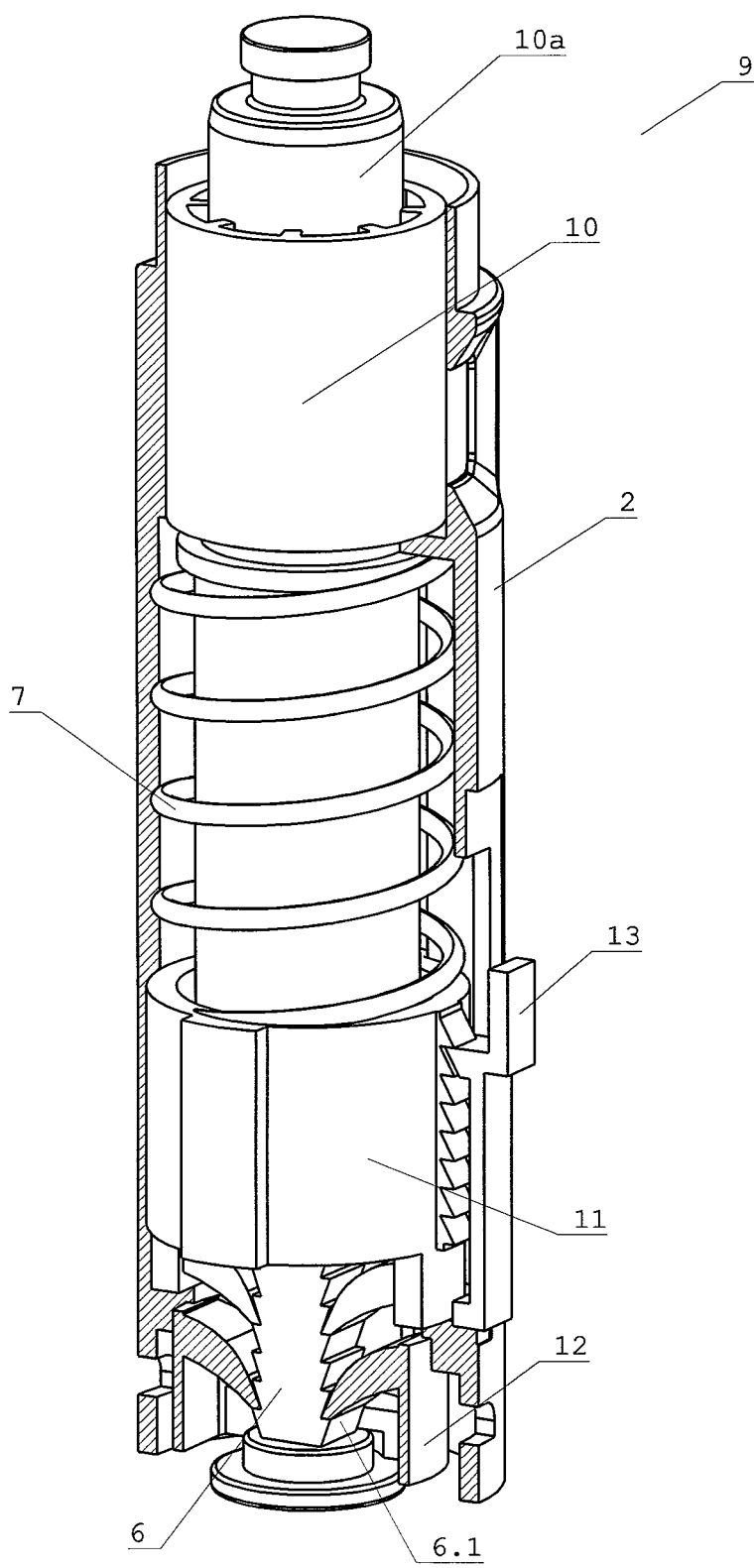
FIG. 4 shows a perspective partially sectional view of the drive-control system according to the first embodiment.
Figure 8A:
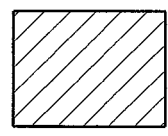
FIGS. 8a, 8b and 8c show alternative cross-sections of the piston rod.
Figure 8B:
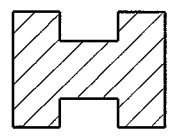
Figure 8C:
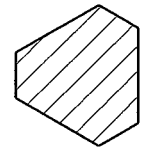

FIG. 4 shows a perspective partially sectional view of the drive-control system 9 according to the first embodiment of the invention. In the system 9 according to the invention, the piston rod 6 is immobilized during setting of a dose, and during delivery of the dose it is advanced outside the housing body 2 into the pharmaceutical substance containing cartridge enclosure 3, causing the set dose to be dispensed. In the described embodiment the piston rod 6 has a rectangular cross-section and transversal ratchet teeth 6.1 are formed on its two opposite side walls. The ratchet teeth 6.1 are directed proximally in the system 9 (towards upside in FIG. 4). The ratchet teeth 6.1 may be formed on at least one side wall of the piston rod 6, or optionally on all the four side walls. Also, the piston rod 6 may have a different cross-section provided that it comprises at least one side wall having transversal ratchet teeth directed proximally formed thereon. Exemplary cross-sections of the piston rod 6 are shown in FIGS. 8a-8c.

Inside the housing body 2, at its distal end 2b the blocking member is located having a form of the blocking sleeve 12 fixed to the housing body 2. The blocking sleeve 12 is provided with two opposite resilient pawls 12.1 engaging the ratchet teeth 6.1 so as to block the translation of the piston rod 6 along the axis A-A in the proximal direction of the system 9. The number of the resilient pawls 12.1 corresponds to the number of the side walls of the piston rod 6 with the ratchet teeth 6.1 formed thereon, i.e. there is at least one pawl 12.1. A man skilled in the art will select a suitable material for the blocking sleeve 12 and the resilient pawls 12.1 as well as the shape of the pawls 12.1 so as to ensure that their functions are accomplished. In the described embodiment, the resilient pawls 12.1 constitute an integral part of the blocking sleeve 12, but they may also be attached to the sleeve 12 in any suitable way.

Figure 5:
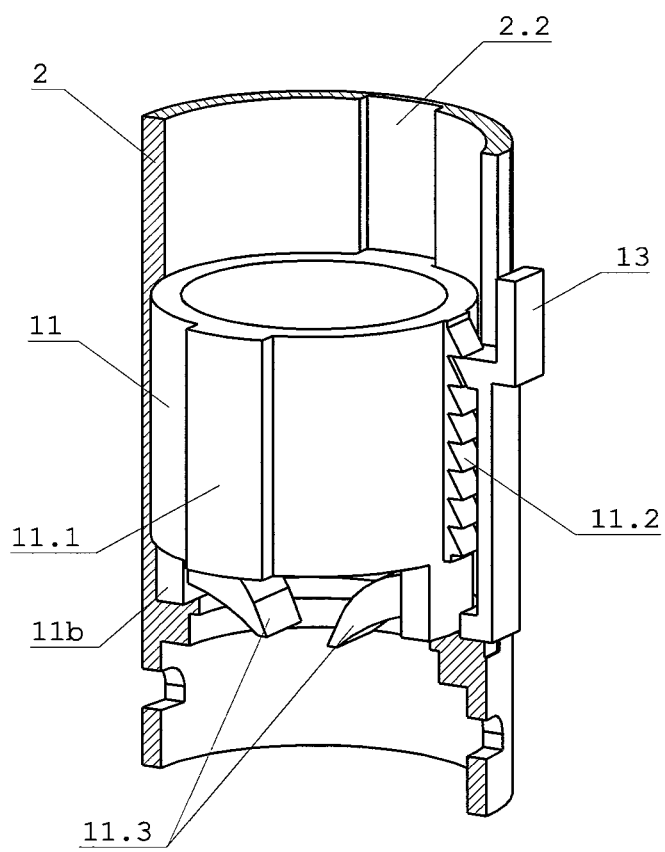
FIG. 5 shows a perspective partially sectional view of selected parts of the drive-control system according to the invention.

In FIG. 5 a perspective partially sectional view of the setting sleeve 11 is shown. As shown in particular in FIGS. 4 and 5, on the outside surface of the setting sleeve 11 there are two guiding means 11.1 extending along the axis A-A of the device. The setting sleeve 11 may have any number (at least one) of guiding means 11.1. Each guiding means 11.1 engages with a corresponding complementary guiding means 2.2 located on the internal wall of the housing body 2. In the described embodiment two guiding means 11.1 having a form of protrusions engage with two grooves 2.2 on the internal wall of the housing body 2. The guiding means 11.1 and 2.2 allow the setting sleeve 11 to move along the axis A-A in relation to the housing body 2 and prevent mutual rotation of both elements in relation to each other.

In the described embodiment the setting sleeve 11 further comprises a series of transversal ratchet teeth 11.2 extending along the axis A-A on its inside surface. The ratchet teeth 11.2 are directed distally in the system 9 (towards downside in FIG. 5). The number of the ratchet teeth 11.2 depends of the number of the doses foreseen to be set and dispensed.

The setting sleeve 11 is further provided with two opposite resilient pawls 11.3 projecting form its distal end 11b. The resilient pawls 11.3 engage with the ratchet teeth 6.1 of the piston rod 6. As in the case of the resilient pawls 12.1, the number of the resilient pawls 11.3 corresponds to the number of the side walls of the piston rod 6 with the ratchet teeth 6.1 formed thereon, i.e. there is at least one pawl 12.1. The resilient pawls 11.3 are shaped so as engage the ratchet teeth 6.1 (which are directed proximally in the system 9) and to allow distal translation of the piston rod 6 and to prevent its translation proximally in the system 9. A man skilled in the art will select a suitable material for the setting sleeve 11 and the resilient pawls 11.3 as well as the shape of the pawls 11.3 so as to ensure that their functions are accomplished. In the described embodiment, the resilient pawls 11.3 constitute an integral part of the setting sleeve 11, but they may also be attached to the sleeve 11 in any suitable way.

An internal thread 11.4 (see FIG. 1) is formed inside the setting sleeve 11 for rotational engagement with an external thread 10.1 formed at the distal end 10b of the control sleeve 10.

Figure 6:
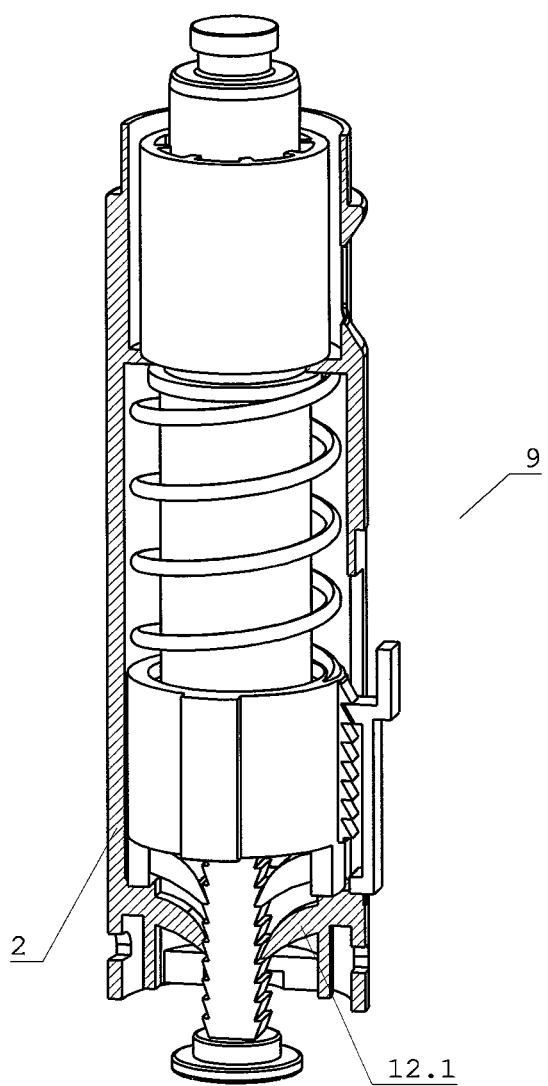
FIG. 6 shows a perspective partially sectional view of the drive-control system according to a second embodiment of the invention.

In FIG. 6 a perspective partially sectional view of the drive-control system 9 according to a second embodiment of the invention is shown. It differs from the above described first embodiment only in that the blocking member is not a sleeve 12 but it is integrated in the housing body 2 and comprises two resilient pawls 12.1 projecting from the inside surface of the housing body 2.

As shown in the figures, the housing body 2 is provided with a resilient element 13 projecting on the outside of the housing body 2. In the described embodiments the resilient element has a form of an arm 13 with an extension 13.1 directed towards the housing body 2, to be engaged with the successive teeth 11.2 of the setting sleeve 11.

Operation of the drive-control system 9 according to the invention is illustrated in FIGS. 7a, 7b, 7c and 7d.

Figure 7A:
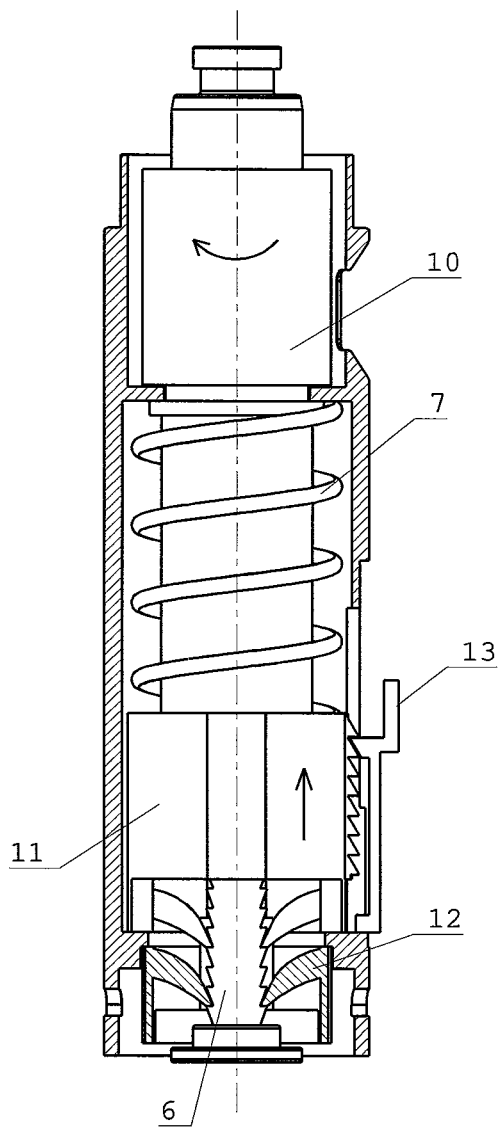
FIGS. 7a, 7b, 7c and 7d show successive stages of operation of the drive-control system according to the first embodiment.
Figure 7B:
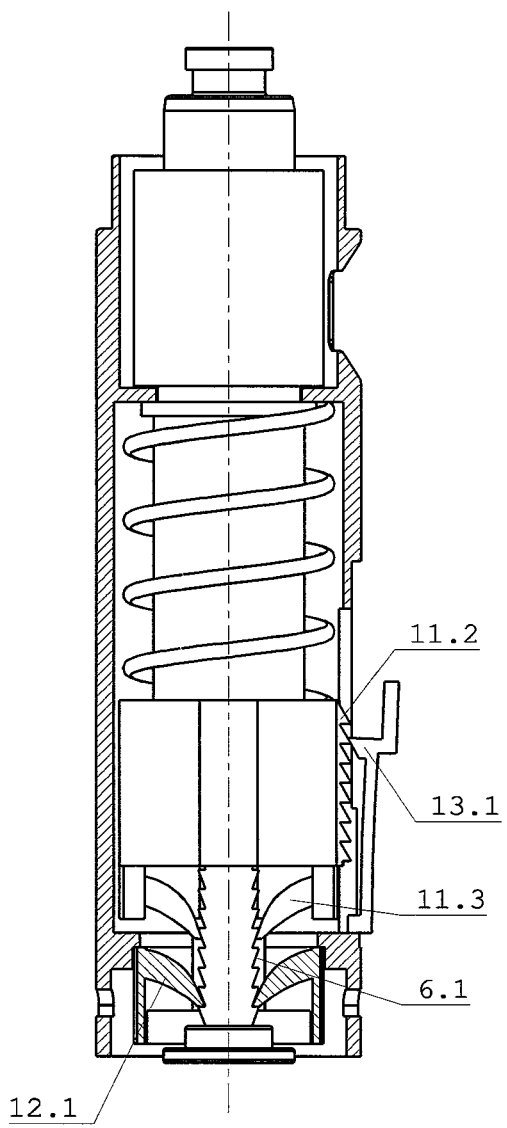

FIG. 7a shows a starting stage in which the whole piston rod 6 is enclosed in the housing body 2 and the setting sleeve 11 is in its initial position close to the distal end 2b of the housing body 2. The setting of a dose is realized by rotation of the control sleeve 10 (indicated by an arrow on FIG. 7a) in a defined direction by a defined angle. Due to the thread engagement 10.1-11.4 of the setting sleeve 11 and the control sleeve 10, the rotation causes the setting sleeve 11 to move over the control sleeve 10. Consequently the setting sleeve 11, being blocked by the guiding means 11.1 and 2.2 and unable to rotate in relation to the housing body 2, advances along the axis A-A proximally in the system 9 (towards upside in FIG. 7a) by a defined pitch defining in turn the set dose. FIG. 7b illustrates a situation during the setting of a dose, i.e. the translation of the setting sleeve 11 causing compression of the spring 7. Considering that during the translation of the setting sleeve 11 its successive teeth 11.2 pass over the extension 13.1 of the resilient element 13, translation of the setting sleeve 11 in the opposite direction is blocked. At the same time, during the proximal translation of the setting sleeve 11, its resilient pawls 11.3 pass over successive teeth 6.1 of the piston rod 6 which may not be translated proximally because it is blocked by the resilient pawls 12.1 of the blocking sleeve 12. The spring 7, which is blocked between the proximal end 11a of the setting sleeve 11 and the projection 2.1 located within the housing body 2, remains compressed as long as the translation of the setting sleeve 11 in the distal direction is blocked.

Figure 7C:
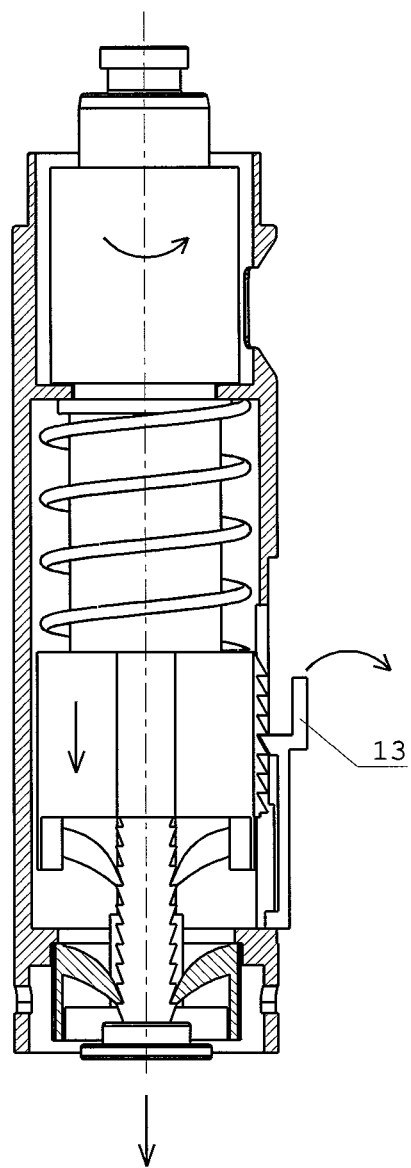

In the situation shown in FIG. 7c, i.e. after the setting sleeve 11 has passed a selected number of the teeth and the dose has been set, the setting sleeve 11 may be unblocked by bending the resilient element 13 as shown by the arrow on FIG. 7c which causes the extension 13.1 to unblock the teeth 11.2 of the setting sleeve 11. Consequently, the setting sleeve 11 is automatically translated distally to its initial position by the force accumulated in the formerly compressed spring 7.

Figure 7D:
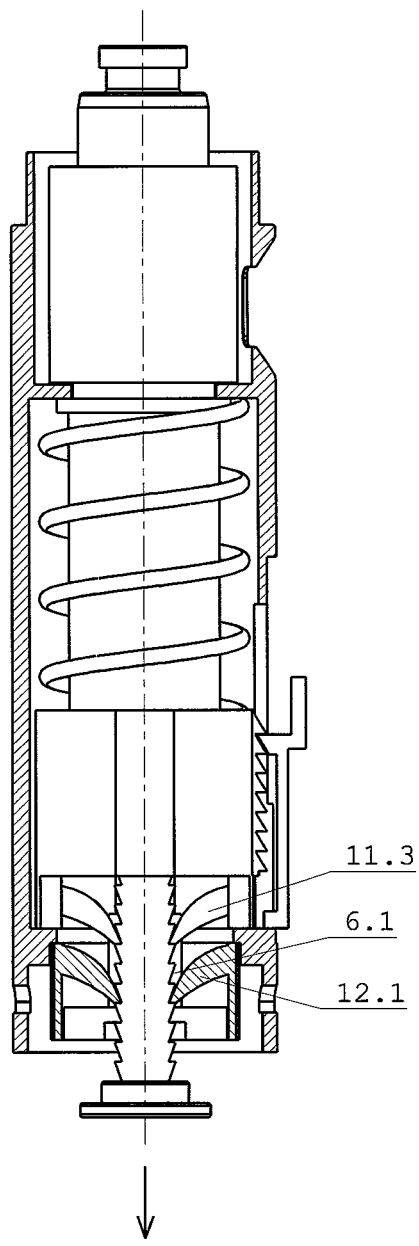

In FIG. 7d a situation is shown when the setting sleeve 11 has returned to its initial position. The pawls 11.3, engaged with the teeth 6.1 of the piston rod 6, have caused its translation out of the housing body 2. At the same time the resilient pawls 12.1 yield under the pressure of the successive teeth 6.1 of the piston rod 6. The translation of the setting sleeve 11 in the distal direction under the force of the extending spring 7 causes rotation of the control sleeve 10 in a direction opposite to its former rotation, back to its initial position. The directions of movement of the control sleeve 10, the setting sleeve 11, the piston rod 6 and the resilient element 13 are indicated by the arrows on FIGS. 7c and 7d. In FIG. 7d the piston rod 6 extends outside the housing body 2 and the resilient element 13 is back to its position of engagement with the teeth 11.2 of the setting sleeve 11.

FIGS. 8a-8c show alternative cross-sections of the piston rod 6.

Figure 9C:
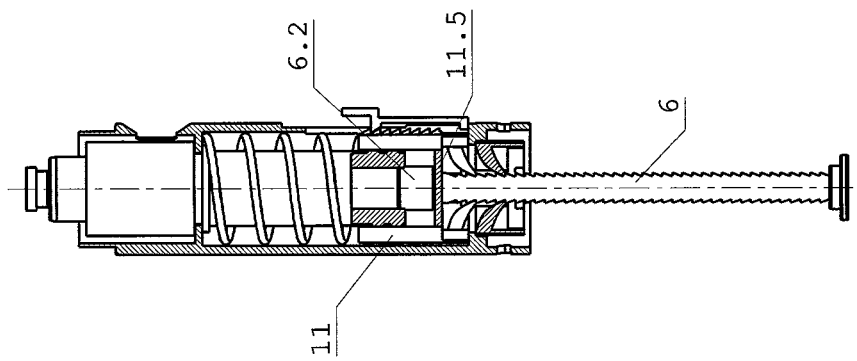
FIGS. 9a, 9b and 9c show partially sectional views of the drive-control system according to a third embodiment of the invention.
Figure 9B:
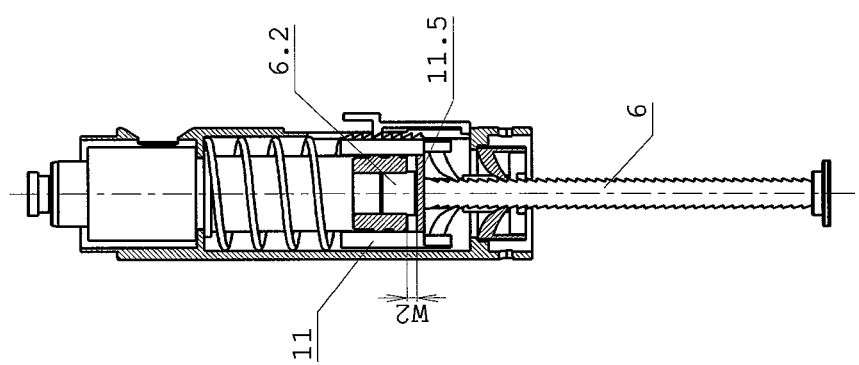
Figure 9A:
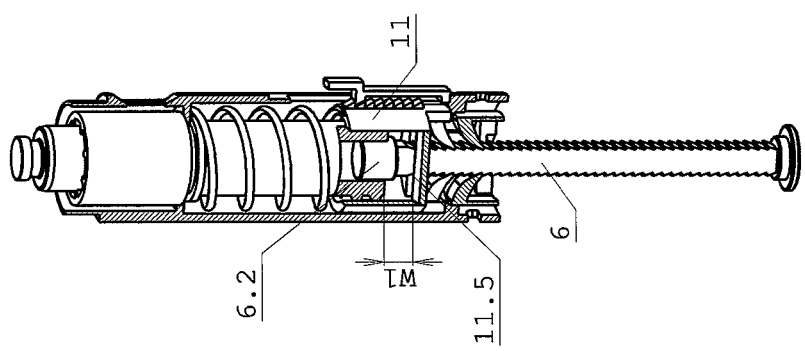

FIGS. 9a, 9b and 9c show partially sectional views of the drive-control system 9 according to a third embodiment of the invention. In this embodiment the setting of a dose after the substance in the cartridge has been exhausted is blocked. As shown in FIGS. 9a-9c, the piston rod 6 and the setting sleeve 11 are provided with mutually cooperating blocking elements 6.2, 11.5 providing blockage of the dose setting and consequently the dose delivery. The operation of the blocking elements 6.2, 11.5 is such that they cooperate to prevent translation of the setting sleeve 11 in the proximal direction once the piston rod 6 has been advanced out of the housing body 2 by a defined distance. The point is to prevent translation of the setting sleeve 11 in the proximal direction and hence further advancement of the piston rod 6 distally to deliver a dose, in a situation when a defined number of doses have already been dispensed from the container 3.

The blocking element 6.2 may have a form of a piston rod head, i.e. a widened proximal ending of the piston rod 6 as seen in FIGS. 9a-9c; optionally it may have a form of any suitable projection or ring etc., located at the proximal ending of the piston rod 6.

The blocking element 11.5 may be constituted by any suitable stop member projecting from the internal wall of the setting sleeve 11 between its pawls 11.3 and its proximal ending. Preferably, it may be a flange with an opening having a shape adapted to the piston rod cross-section allowing the piston rod 6 to pass through it and interfering with the blocking element 6.2 to prevent its passage through.

As mentioned above, the cross-section of a complete device 1 is shown in FIG. 1. As may be seen, the device 1 comprises the drive-control system 9, the triggering activating means 8 and the knob 5.

Figure 10:
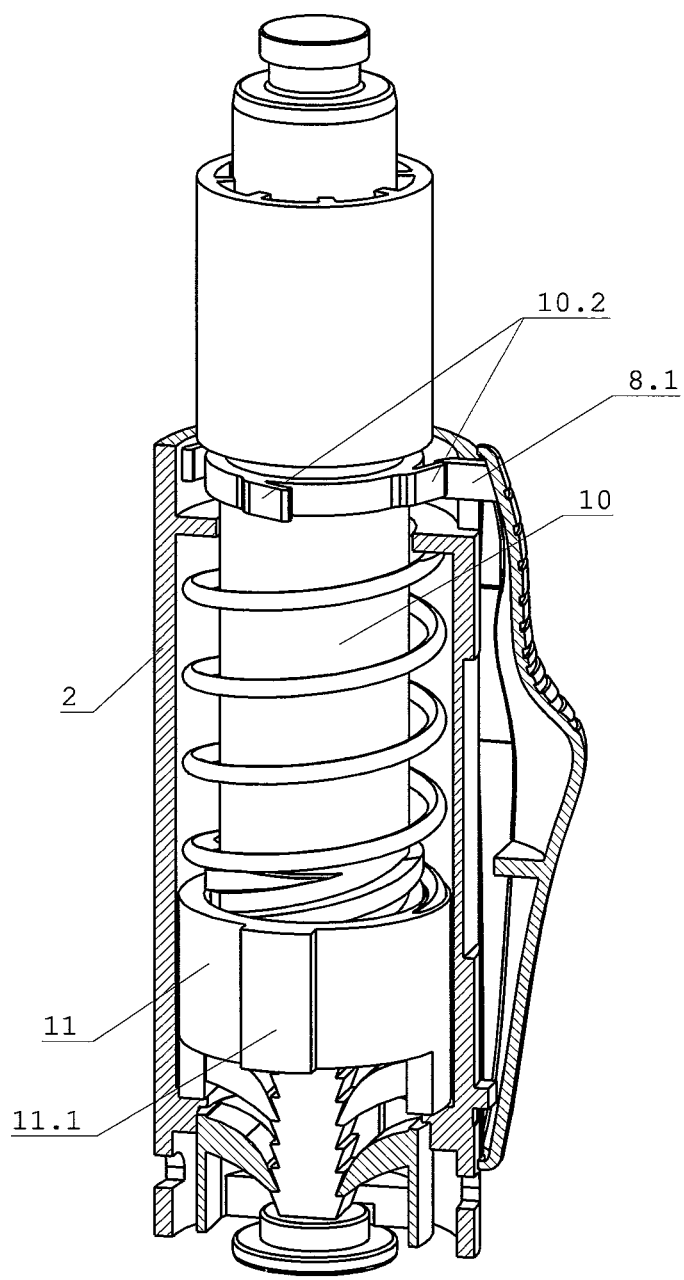
FIG. 10 shows a partially sectional view of the drive-control system according to a fourth embodiment of the invention.

FIG. 10 shows a partially sectional view of the drive-control system according to a fourth embodiment of the invention. In this embodiment the setting of a dose is also realized by rotation of the control sleeve 10 in a defined direction by a defined angle. As in the above described embodiments, the rotation of the control sleeve 10 causes the setting sleeve 11 to move over the control sleeve 10 due to the thread engagement 10.1-11.4 of the setting sleeve 11 and the control sleeve 10. Consequently the setting sleeve 11, being blocked by the guiding means 11.1 and 2.2 and unable to rotate in relation to the housing body 2, advances along the axis A-A proximally in the system 9 by a defined pitch defining in turn the set dose, causing compression of the spring 7. However, in this embodiment the setting sleeve 11 does not have the series of the blocking teeth 11.2. Instead, the distance by which the setting sleeve 11 is translated proximally is defined by the angle of rotation of the control sleeve 10. To achieve this aim, the control sleeve 10 is provided with dedicated blocking elements 10.2. As shown in FIG. 10, the blocking elements 10.2 may have a form of ratchets integral with the control sleeve 10 or attached thereto. The blocking elements 10.2 are distributed around the control sleeve 10 and have a shape adapted to cooperate with the triggering activating means of the injection device according to the invention. The triggering activating means is provided with an extension 8.1. The cooperation of the ratchet 10.2 with the extension 8.1 consists in that during the setting of a dose, the control sleeve 10 may be rotated by a desired angle until a respective ratchet 10.2 passes over the extension 8.1. The number of ratchets 10.2 corresponds to the number of doses available in the injection device. Translation of the triggering activating means along the housing body 2 in the distal direction causes the ratchet to be unblocked which allows the control sleeve 10 to be rotated in a direction opposite to the setting of dose direction. In consequence, the piston rod 6 is advanced out and the dose is delivered. The described embodiment may also be realized as a reversed variant, i.e. the ratchet may be located on the triggering activating means and the control sleeve 10 may be provided with extensions instead of the ratchets (not shown).

Figure 11:
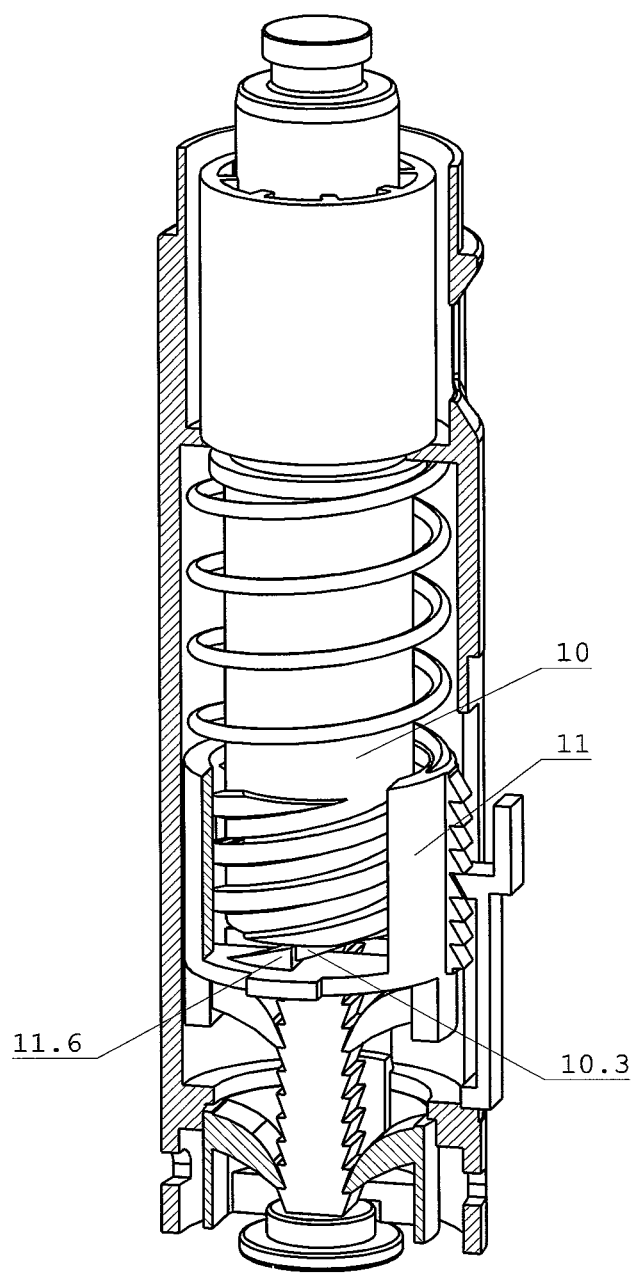
FIG. 11 shows another partially sectional view of the drive-control system according to the invention.

FIG. 11 shows a preferred embodiment of the limitation of rotation of the control sleeve 10 and the translation of the setting sleeve 11. As shown, projections 10.3 and 11.6 are provided respectively at the distal end of the control sleeve 10 and inside the setting sleeve 11. In a determined position the projections 10.3 and 11.6 abut each other and prevent further rotation of the setting sleeve 11. More than one projections 10.3 and 11.6 respectively may be foreseen. In another variant, the function of blocking the rotation of the control sleeve 10 in a certain position may be accomplished by end surface of the control sleeve 10 coming into contact with the blocking element 11.5 shown in FIGS. 9a-9c. However, the variant with the projections 10.3 and 11.6 is preferred because it enables a more precise stoppage of the control sleeve 10 rotation.

The operation of the device is as follows.

The setting of a dose of the pharmaceutical substance to be delivered is done by the turning the knob 5 in the appropriate direction; the rotation activates the drive-control system 9 i.e. the rotation of the control sleeve 10 and the consequent movements of specific components of the system, as described with reference to FIGS. 7a and 7b. Passing over one teeth 11.2 of the setting sleeve 11 and respectively one teeth 6.1 of the piston rod 6 may correspond to setting one unitary dose of the pharmaceutical substance. By turning the knob 5 further the user may set a larger dose which is a multiple of the unitary dose.

The setting of a dose is done in a situation when the triggering activating means 8 is a position of engagement of the resilient member 13 with the teeth 11.2 of the setting sleeve 11.

The injection of the pharmaceutical substance is done by pushing the triggering activating means 8 in a defined direction along the housing body 2. In the embodiments shown in FIGS. 1-9 the triggering activating means 8 is translated distally which causes the resilient member 13 to deform and dis-engage from the teeth 11.2 of the setting sleeve 11. Due to the action of the compressed spring 7 the setting sleeve 11 is automatically translated in the distal direction of the device, i.e. returns to its initial position causing the piston rod 6 to be advanced distally out of the housing body 2. As the piston rod 6 is advanced out of the housing body 2a it moves into the cartridge 3 and expels the dose of the pharmaceutical substance therefrom. The device is preferably provided with a feature allowing blockage of the setting of a dose after the pharmaceutical substance in the cartridge has been exhausted.

In the embodiment shown in FIG. 10 the translation of the triggering activating means 8 in the distal direction causes the blocking element 10.2 to be released and in consequence the rotation of the control sleeve 10, the translation of the setting sleeve 11 and the distal translation of the piston rod 6.

The invention claimed is:

1. A drive-control system for an injection device for delivering a settable dose of a pharmaceutical substance contained in a cartridge enclosure, the system comprising a tubular housing body having a longitudinal axis, a proximal end and a distal end connectable to the cartridge enclosure, the system further comprising a helical spring contained in the housing body and a piston rod extending along the longitudinal axis and moveable towards said distal end and blocked in translation towards the proximal end, characterized in that the housing body further contains a control sleeve on which the spring is mounted, the control sleeve being rotatable around the axis, and a setting sleeve translatable along the axis, wherein the control sleeve is threadably connected at its distal end to the setting sleeve;
the setting sleeve is engaged with the internal wall of the housing body in a way preventing rotation of the setting sleeve in relation to the housing body,
the setting sleeve is engaged with the piston rod by at least one series of ratchet teeth on the piston rod directed towards the proximal end of the housing body and at least one resilient pawl on the setting sleeve engaging the ratchet teeth of the piston rod, in a way enabling the translation of the setting sleeve towards the proximal end of the housing body and blocking the translation of the setting sleeve in the opposite direction in relation to the piston rod;
a blocking member is provided on the distal end of the housing body, the blocking member being engaged with the piston rod by the at least one series of ratchet teeth and at least one resilient pawl on the blocking member engaging the ratchet teeth of the piston rod so as to block the translation of the piston rod 6 in the proximal direction, whereby
rotation of the control sleeve in a first direction causes compression of the spring and translation of the setting sleeve towards the proximal end of the housing body, and extension of the spring causes translation of the setting sleeve towards the distal end of the housing body, rotation of the control sleeve in a second direction and translation of the piston rod towards the outside of the housing body.

2. The system according to claim 1, wherein the setting sleeve is engaged with the internal wall of the housing body at least one pair of complementary longitudinal guiding means.

3. The system according to claim 2, wherein the at least one pair of complementary longitudinal guiding means consists of a longitudinal groove located on the internal wall of the housing body and a longitudinal protrusion located on the external wall of the setting sleeve.

4. The system according to claim 1, wherein the piston rod has a rectangular cross-section and the series of ratchet teeth is located on its side wall.

5. The system according to claim 1, wherein the blocking member has a form of a blocking sleeve located inside the housing body, the piston rod extending through the blocking sleeve.

6. The system according to claim 5, characterized in that the at least one resilient pawl is integral with the setting sleeve.

7. The system according to claim 1, wherein the blocking member has a form of a blocking sleeve located inside the housing body, the piston rod extending through the blocking sleeve, and the at least one resilient pawl is integral with the blocking sleeve.

8. The system according to claim 1, wherein the piston rod and the setting sleeve are provided with mutually cooperating blocking elements preventing the setting sleeve to be translated proximally when the piston rod extends out of the housing body by a defined distance.

9. The system according to claim 8, wherein the blocking element of the piston rod is selected from a group comprising an enlarged proximal ending of the piston rod, a projection located at the proximal ending of the piston rod and an annular flange located at the proximal ending of the piston rod.

10. The system according to claim 8, wherein the blocking element of the setting sleeve is a stop member projecting from the inside wall of the setting sleeve between the pawls and the proximal end of the setting sleeve.

11. The system according to claim 1, wherein the setting sleeve comprises means for engagement of the setting sleeve with the housing body and the housing body comprises a resilient element, the engagement means cooperating with the resilient element to selectively block and release the translation of the setting sleeve along the housing body.

12. The system according to claim 11, wherein the engagement means of the setting sleeve has a form of a series of ratchet teeth that are perpendicular to the axis and directed towards the distal end of the housing body, and the resilient element of the housing body is an arm comprising an extension to be engaged with the teeth.

13. The system according to claim 1, wherein the control sleeve comprises at least one blocking element enabling rotation of the control sleeve in relation to the housing body in one direction as well as selective blocking and releasing the rotation of the control sleeve in the opposite direction.

14. The system according to claim 13, wherein the at least one blocking element has a form of a ratchet cooperating with a triggering activating means arranged on the housing body.

15. The system according to claim 13, wherein the at least one blocking element has a form of a projection cooperating with a ratchet of a triggering activating means arranged on the housing body.

16. An injection device for delivering a settable dose of a liquid pharmaceutical substance, adapted to be coupled with a cartridge enclosure containing said substance, the distal end of the cartridge enclosure being adapted to be coupled with a disposable injection means, wherein the injection device comprises the drive-control system according to claim 1, and wherein the housing body comprises the triggering activating means and a knob, the triggering activating means and the knob cooperating with the drive-control system;

the knob is engaged with the rotatable control sleeve to enable the rotation of the control sleeve in a defined direction;

the triggering activating means enabling selective blocking and releasing of the translation of the setting sleeve towards the distal end of the housing body, wherein when said translation is blocked, the setting sleeve may be translated towards the proximal end of the housing body and when the setting sleeve is released it is translated towards the distal end of the housing body by the action of the extending spring.

17. The device according to claim 16, wherein the triggering activating means cooperating with the resilient element of the housing body is adapted to be placed in a first and a second position, the first position being the position of engagement of the triggering activating means with the setting sleeve by the extension and the second position being the position of disengagement of the triggering activating means with the setting sleeve.

18. An injection device for delivering a settable dose of a liquid pharmaceutical substance, adapted to be coupled with a cartridge containing said substance, the distal end of the cartridge being adapted to be coupled with a disposable injection means, wherein the injection device comprises the drive-control system according to claim 12, and wherein the housing body comprises the triggering activating means and a knob, the triggering activating means and the knob cooperating with the drive-control system;

the knob is engaged with the rotatable control sleeve to enable the rotation of the control sleeve in a defined direction;

the triggering activating means cooperates with the blocking element of the control sleeve to enable selective blocking and releasing rotation of the control sleeve in relation to the housing body in a first direction, said rotation being combined with proximal translation of the setting sleeve, and enabling rotation of the control sleeve in a second opposite direction, said direction being combined with translation of the setting sleeve towards the distal end of the housing body by the action of the extending spring.

19. The device according to claim 18, wherein the triggering activating means comprises an extension cooperating with the blocking element of the control sleeve, the blocking element being adapted to be placed in a first and a second position, the first position being the position of engagement of the extension with the blocking element and the second position being the position of disengagement of the extension with the blocking element.

* * * * *